US011617902B2

(12) United States Patent
Zacharopoulos

(10) Patent No.: US 11,617,902 B2
(45) Date of Patent: Apr. 4, 2023

(54) MODULATED RADIATION BEAM ALIGNMENT FOR MEDICAL LINEAR ACCELERATOR

(71) Applicant: AKTINA CORP., Congers, NY (US)

(72) Inventor: Nicholas G. Zacharopoulos, West Nyack, NY (US)

(73) Assignee: Aktina Corp., Congers, NY (US)

( * ) Notice: Subject to any disclaimer, the term of this patent is extended or adjusted under 35 U.S.C. 154(b) by 0 days.

(21) Appl. No.: 17/407,629

(22) Filed: Aug. 20, 2021

(65) Prior Publication Data

US 2022/0062658 A1 Mar. 3, 2022

Related U.S. Application Data

(60) Provisional application No. 63/070,456, filed on Aug. 26, 2020.

(51) Int. Cl.
*A61N 5/10* (2006.01)

(52) U.S. Cl.
CPC ........ *A61N 5/1049* (2013.01); *A61N 5/1047* (2013.01); *A61N 5/1081* (2013.01); *A61N 2005/1051* (2013.01)

(58) Field of Classification Search
None
See application file for complete search history.

(56) References Cited

U.S. PATENT DOCUMENTS

| 9,192,784 | B1 | 11/2015 | Ritt et al. | |
| 2014/0094643 | A1* | 4/2014 | Gall | A61N 1/44 600/1 |
| 2015/0093011 | A1 | 4/2015 | Gaudio | |
| 2018/0250531 | A1* | 9/2018 | Ansorge | G01N 23/20 |

FOREIGN PATENT DOCUMENTS

EP 3202458 A2 8/2017

OTHER PUBLICATIONS

P. Rowshanfarzad et al., "Isocenter verification for linac-based stereotactic radiation therapy: review of principles and techniques", Journal of Applied Clinical Medical Physics, vol. 12, No. 4, Nov. 15, 2011, XP055168728, 10 pages.

* cited by examiner

*Primary Examiner* — Hoon K Song
(74) *Attorney, Agent, or Firm* — Rothwell, Figg, Ernst & Manbeck, P.C.

(57) ABSTRACT

Systems and methods for delivering a radiation beam using a linear accelerator (LINAC). Optimal beam alignment parameters may be determined and stored for each of N gantry angles. The beam alignment parameters may adjust a current supplied to one or more bending magnets of the LINAC and, thus, change an angle and direction of the radiation beam. An optimum beam alignment parameter for a gantry angle may be determined by adjusting the beam alignment parameter until a center of a radiation field of the radiation beam in a radiation transmission image is at a center of shadow of a radiation opaque marker, which may be placed at a radiation isocenter. The beam alignment parameters stored for the N gantry angles may be used to adjust the beam steering current as the gantry is rotated through any arbitrary gantry angle.

20 Claims, 12 Drawing Sheets

MODULATED RADIATION BEAM ALIGNMENT FOR MEDICAL LINEAR ACCELERATOR

CROSS-REFERENCE TO RELATED APPLICATION

The present application claims the benefit of priority to U.S. Provisional Patent Application Ser. No. 63/070,456, filed on Aug. 26, 2020, which is incorporated herein by reference in its entirety.

BACKGROUND

Field of Invention

The present invention relates generally to radiation therapy in which a medical linear accelerator (LINAC) delivers a radiation beam to a precise point within a patient.

Discussion of the Background 1.1. Mechanical Rotations

Radiation therapy is a type of cancer treatment that uses beams of intense high energy radiation beams to kill cancer cells. During treatment, as shown in FIGS. 1 and 2, a gantry 102 of a medical linear accelerator (LINAC) 100 delivers the radiation beams 104 to a precise point within a patient (not shown) supported on a couch 106. During the treatment, the gantry 102 of the LINAC 100 rotates to different gantry angles including, for example, 0° and 180°, as shown in FIGS. 1 and 2, respectively. The geometrical accuracy of LINAC mechanical rotations affects the accuracy of the treatment.

1.2 Radiation Isocenter

The radiation isocenter is the point in space where the radiation beams intersect when the gantry rotates. A proper determination of the radiation isocenter point in space may enhance the accuracy of the patient treatment. With the patient positioned so that a tumor is located at the radiation isocenter, the radiation beams will be fixed at the tumor through gantry. If the radiation isocenter is incorrectly defined and/or if the tumor is not correctly placed at isocenter, high doses of radiation may be delivered outside the tumor, which may create unwanted adverse side effects.

1.3 Gantry Rotation Mechanical Errors

As the gantry 102 of the LINAC 100 rotates, the gantry 102 tends to translate under its own weight. Often the gantry 102 tends to translate in and out of an idealized gantry plane of rotation. The amount and direction of this translation is dependent on the gantry angle and the LINAC mechanical design. An example of the translation is shown in FIG. 3, which provides a side view of the LINAC 100 shown with the gantry 102 at an angle of 0° as well as a superimposed view of the gantry 102 at an angle of 180°. The axes of the radiation beams 104 from with the gantry 102 at the angles of both of 0° and 180° are shown with dotted lines. The spread of the two axes of the radiation beam 104 is due to the LINAC gantry sag, which causes translation forward or backward as the gantry 102 rotates. Typically, little can be done to reduce these mechanical errors, and the mechanical errors are currently accepted as an inaccuracy in the patient's treatment.

SUMMARY

Aspects of the invention may correct for gantry errors using modulated beam alignment. In some aspects, a linear accelerator (LINAC) may modulate a beam electro-magnet current at each gantry position to compensate for mechanical errors in the gantry by changing the direction of the beam so that the central axis of the beam is points at the same location in space at every gantry angle.

One aspect of the invention may provide a method including using one or more bending magnets and a collimator of a linear accelerator (LINAC) to generate a radiation beam. The method may include using the LINAC to position a gantry at a first gantry angle. The method may include, with the gantry positioned at the first gantry angle, acquiring a first radiation transmission image indicative of a radiation field of the radiation beam after passing by a radiation opaque marker. The method may include using the first radiation transmission image to determine a center of the radiation field of the radiation beam and a center of a shadow of the radiation opaque marker in the radiation field of the radiation beam. The method may include using the LINAC to determine that the center of the radiation field of the radiation beam is not at the center of the shadow of the radiation opaque marker. The method may include, if the center of the radiation field of the radiation beam is determined to not be at the center of the shadow of the radiation opaque marker, adjusting the radiation beam by adjusting a beam alignment parameter and repeating the radiation transmission image acquisition step and the centers determination step with the adjusted radiation beam and the gantry positioned at the first gantry angle until a center of the radiation field of the adjusted radiation beam is determined to be at the center of the shadow of the radiation opaque marker, wherein adjusting the beam alignment parameter adjusts a current supplied by the LINAC to the one or more bending magnets. The method may include, if the center of the radiation field of the adjusted radiation beam is determined to be at the center of the shadow of the radiation opaque marker, using the LINAC to store the adjusted beam alignment parameter as an optimal beam alignment parameter for the first gantry angle. The method may include, using the adjusted beam alignment parameter stored as the optimal beam alignment parameter for the first gantry angle to adjust the current supplied by the LINAC to the one or more bending magnets when the gantry of the LINAC rotates to the first gantry angle.

In some aspects, the method may further include positioning the radiation opaque marker. In some aspects, the method may further include positioning the radiation opaque marker at a radiation isocenter, and the radiation isocenter may be a point in space where radiation beams generated by the LINAC interest when the gantry of the LINAC rotates. In some aspects, the method may further include determining the radiation isocenter.

In some aspects, the method may further include using an electronic portal imaging device (EPID) to generate the first radiation transmission image based on radiation received by the EPID. In some aspects, the radiation opaque marker may be a spherical radiation opaque marker. In some aspects, the radiation field of the radiation beam may be a square radiation beam.

In some aspects, using the LINAC to determine that the center of the radiation field of the radiation beam is not at the center of the shadow of the radiation opaque marker may include: determining a distance between the center of the radiation field of the radiation beam and the center of the shadow of the radiation opaque marker; and determining that the distance is greater than a distance tolerance threshold. In some aspects, using the LINAC to determine that the center of the radiation field of the adjusted radiation beam is at the center of the shadow of the radiation opaque marker may include: determining a distance between the center of the radiation field of the adjusted radiation beam and the center of the shadow of the radiation opaque marker; and determining that the distance is less than a distance tolerance threshold.

In some aspects, the adjusted beam alignment parameter may be stored as the optimal beam alignment parameter for the first gantry angle in a lookup table.

In some aspects, the method may further include using the LINAC to position the gantry at a second gantry angle. In some aspects, the method may further include, with the gantry positioned at the second gantry angle, acquiring a second radiation transmission image indicative of the radiation field of the radiation beam after passing by the radiation opaque marker. In some aspects, the method may further include using the second radiation transmission image to determine a center of the radiation field of the radiation beam and a center of a shadow of the radiation opaque marker in the radiation field of the radiation beam; using the LINAC to determine that the center of the radiation field of the radiation beam is not at the center of the shadow of the radiation opaque marker. In some aspects, the method may further include, if the center of the radiation field of the radiation beam is determined to not be at the center of the shadow of the radiation opaque marker, adjusting the radiation beam by adjusting a beam alignment parameter and repeating the radiation transmission image acquisition step and the centers determination step with the adjusted radiation beam and the gantry positioned at the second gantry angle until a center of the radiation field of the adjusted radiation beam is determined to be at the center of the shadow of the radiation opaque marker. In some aspects, adjusting the beam alignment parameter may adjust the current supplied by the LINAC to the one or more bending magnets. In some aspects, the method may further include, if the center of the radiation field of the adjusted radiation beam is determined to be at the center of the shadow of the radiation opaque marker, using the LINAC to store the adjusted beam alignment parameter as an optimal beam alignment parameter for the second gantry angle. In some aspects, the method may further include using the adjusted beam alignment parameter stored as the optimal beam alignment parameter for the second gantry angle to adjust the current supplied by the LINAC to the one or more bending magnets when the gantry of the LINAC rotates to the second gantry angle.

In some aspects, the method may further include, for each of N gantry angles: using the LINAC to position the gantry at a gantry angle of the N gantry angles; determining an optimal beam alignment parameter for the gantry angle of the N gantry angles, wherein the optimal beam alignment parameter adjusts the current supplied by the LINAC to the one or more bending magnets such that a center of the radiation field of the radiation beam is at a center of the radiation opaque marker when the gantry is at the gantry angle of the N gantry angle; and storing the optimal beam alignment parameter for the gantry angle of the N gantry angles. In some aspects, the method may further include using the N optimal beam alignment parameters stored for the N gantry angles to adjust the current supplied by the LINAC to the one or more bending magnets during rotation of the gantry. In some aspects, the method may further include: using the LINAC to determine a formula for determining beam alignment parameters based on the N optimal beam alignment parameters stored for the N gantry angles; and using the LINAC to adjust the current supplied by the LINAC to the one or more bending magnets based on the formula as the gantry rotates. In some aspects, the LINAC may employ parametric curve fitting or interpolation to determine the formula.

In some aspects, the method may further include using the LINAC to position the collimator at least at a first collimator angle and a second collimator angle. In some aspects, the first radiation transmission image may be acquired with the gantry positioned at the first gantry angle and the collimator position at the first collimator angle. In some aspects, the second collimator angle is different than the first collimator angle. In some aspects, the method may further include, with the gantry positioned at the first gantry angle and the collimator positioned at the second collimator angle, acquiring an additional radiation transmission image indicative of a radiation field of the radiation beam after passing by the radiation opaque marker. In some aspects, the first radiation transmission image and the additional transmission image may be used to determine the center of the radiation field of the radiation beam. In some aspects, the LINAC may determine the center of the radiation field of the radiation beam by averaging the center of the radiation field in the first radiation transmission field image and the center of the radiation field in the additional radiation transmission field image.

Another aspect of the invention may provide a linear accelerator (LINAC) comprising: a gantry, one or more bending magnets, a collimator, and a controller. The controller may be configured to cause the LINAC to use the one or more bending magnets and the collimator to generate a radiation beam. The controller may be configured to cause the LINAC to position the gantry at a first gantry angle. The controller may be configured to cause the LINAC to, with the gantry positioned at the first gantry angle, acquire a first radiation transmission image indicative of a radiation field of the radiation beam after passing by a radiation opaque marker. The controller may be configured to cause the LINAC to use the first radiation transmission image to determine a center of the radiation field of the radiation beam and a center of a shadow of the radiation opaque marker in the radiation field of the radiation beam. The controller may be configured to cause the LINAC to determine that the center of the radiation field of the radiation beam is not at the center of the shadow of the radiation opaque marker. The controller may be configured to cause the LINAC to, if the center of the radiation field of the radiation beam is determined to not be at the center of the shadow of the radiation opaque marker, adjust the radiation beam by adjusting a beam alignment parameter and repeat the radiation transmission image acquisition step and the centers determination step with the adjusted radiation beam and the gantry positioned at the first gantry angle until a center of the radiation field of the adjusted radiation beam is determined to be at the center of the shadow of the radiation opaque marker, and adjusting the beam alignment parameter may adjust a current supplied to the one or more bending magnets. The controller may be configured to cause the LINAC to, if the center of the radiation field of the adjusted radiation beam is determined to be at the center of the shadow of the radiation opaque marker, store the adjusted beam alignment parameter as an optimal beam alignment parameter for the first gantry angle. The controller may be configured to cause the LINAC to use the adjusted beam alignment parameter stored as the optimal beam alignment parameter for the first gantry angle to adjust the current supplied by the LINAC to the one or more bending magnets when the gantry of the LINAC rotates to the first gantry angle.

Still another aspect of the invention may provide a method including using one or more bending magnets and a collimator of a gantry of a linear accelerator (LINAC) to generate a radiation beam. The method may include rotating the gantry to each of N gantry angles. The method may include, at each of the N gantry angles, using a beam alignment parameter stored for the gantry angle to adjust a current supplied by the LINAC to the one or more bending magnets, and the beam alignment parameters stored for the N gantry angles correct for mechanical rotation errors of the gantry.

Yet another aspect of the invention may provide a linear accelerator (LINAC) include a gantry and a controller. The gantry may include one or more bending magnets and a collimator. The controller may be configured to use the one or more bending magnets and the collimator of the gantry to generate a radiation beam. The controller may be configured to rotate the gantry to each of N gantry angles. The controller may be configured to, at each of the N gantry angles, use a beam alignment parameter stored for the gantry angle to adjust a current supplied by the LINAC to the one or more bending magnets, and the beam alignment parameters stored for the N gantry angles correct for mechanical rotation errors of the gantry.

Still another aspect of the invention may provide a computer program including instructions for adapting a linear accelerator (LINAC) to perform any of the methods set forth above. Yet another aspect of the invention may provide a carrier containing the computer program, and the carrier may be one of an electronic signal, optical signal, radio signal, or compute readable storage medium.

Still another aspect of the invention may provide a linear accelerator (LINAC) including processing circuitry and a memory. The memory may contain instructions executable by the processing circuitry, whereby the LINAC is operative to perform any of the methods set forth above.

Yet another aspect of the invention may provide a linear accelerator (LINAC) adapted to any of the methods set forth above.

Still another aspect of the invention may provide any combination of the aspects set forth above.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

PARTS LIST

100—linear accelerator (LINAC) 100
102—gantry
104—radiation beam
106—couch
402—waveguide
404—one more bending magnets
406—radiation beam in the one or more bending magnets
408—angle at which the radiation beam is directed onto the target
410—collimator
412—central beam axis
414—superior beam edge
416—inferior beam edge
600—marker assembly
602—radiation opaque marker
604—stem
606—base
902—border of the radiation field
904—border of the marker
1200—controller of LINAC
1202—processing circuitry (PC)
1208—local storage unit
1210—network
1241—computer program product (CPP)
1242—computer readable medium (CRM)
1243—computer program (CP)
1244—computer readable instructions (CRI)
1248—steering current generator
1250—gantry rotator
1252—collimator rotator
1254—radiation beam generator
1255—one or more processors (P)
1265—transmitter (Tx)
1267—receiver (Rx) 1267
1268—network interface

DETAILED DESCRIPTION OF PREFERRED EMBODIMENTS 2.1 Radiation Beam Alignment

Figure 1:
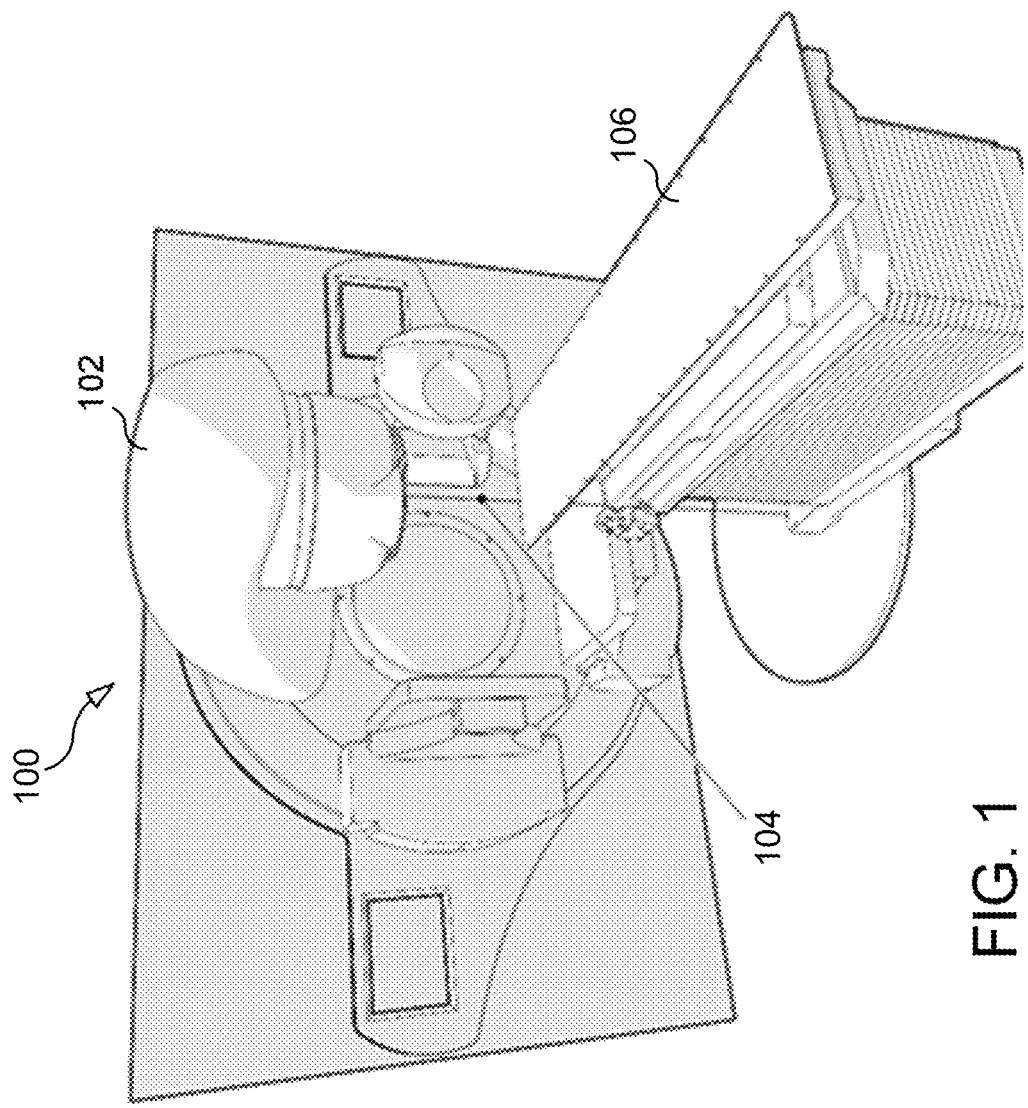
FIG. 1 illustrates a gantry of a medical linear accelerator (LINAC) that has been rotated to a gantry angle of 0° delivering a radiation beam.
Figure 2:
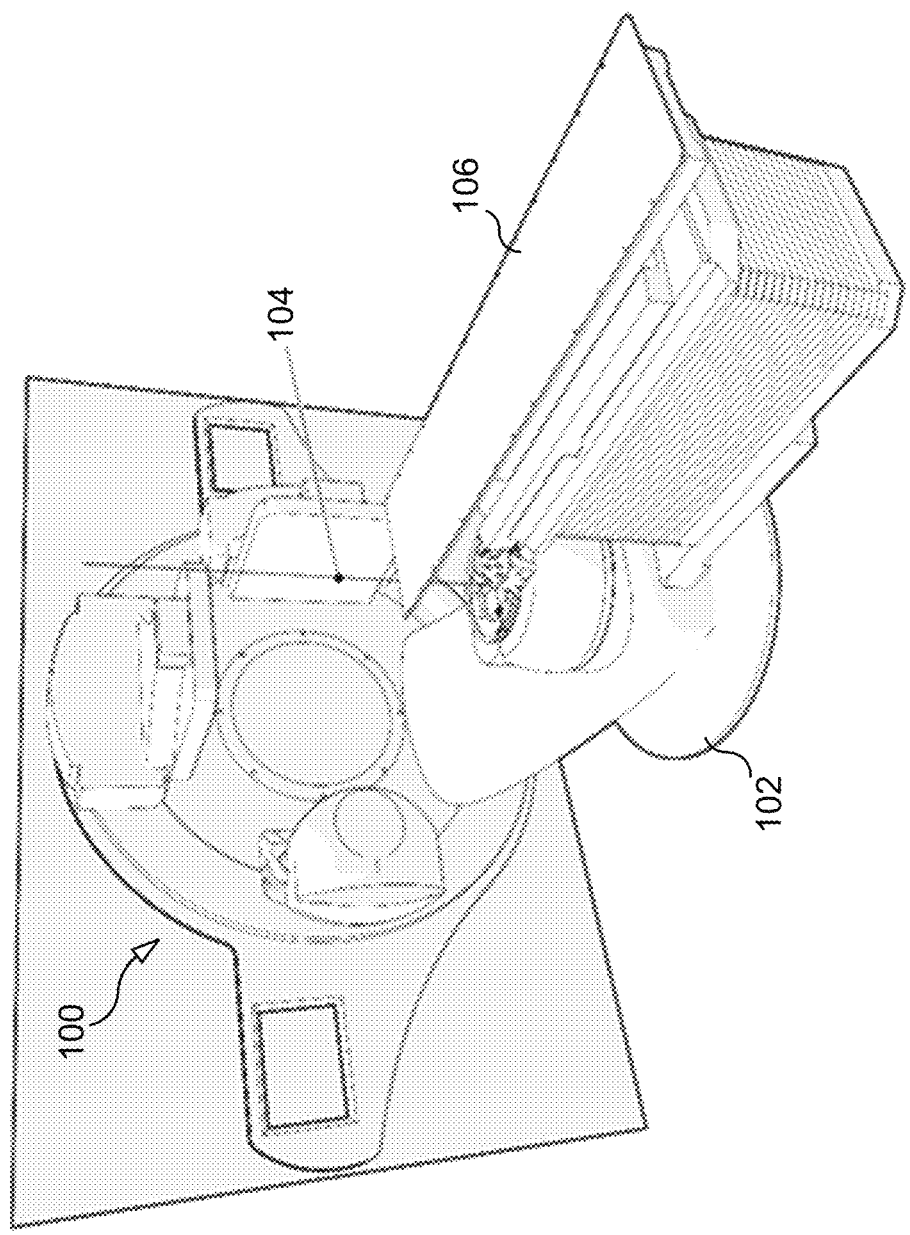
FIG. 2 is illustrates the gantry of the LINAC rotated to a gantry angle of 180° and delivering the radiation beam.
Figure 3:
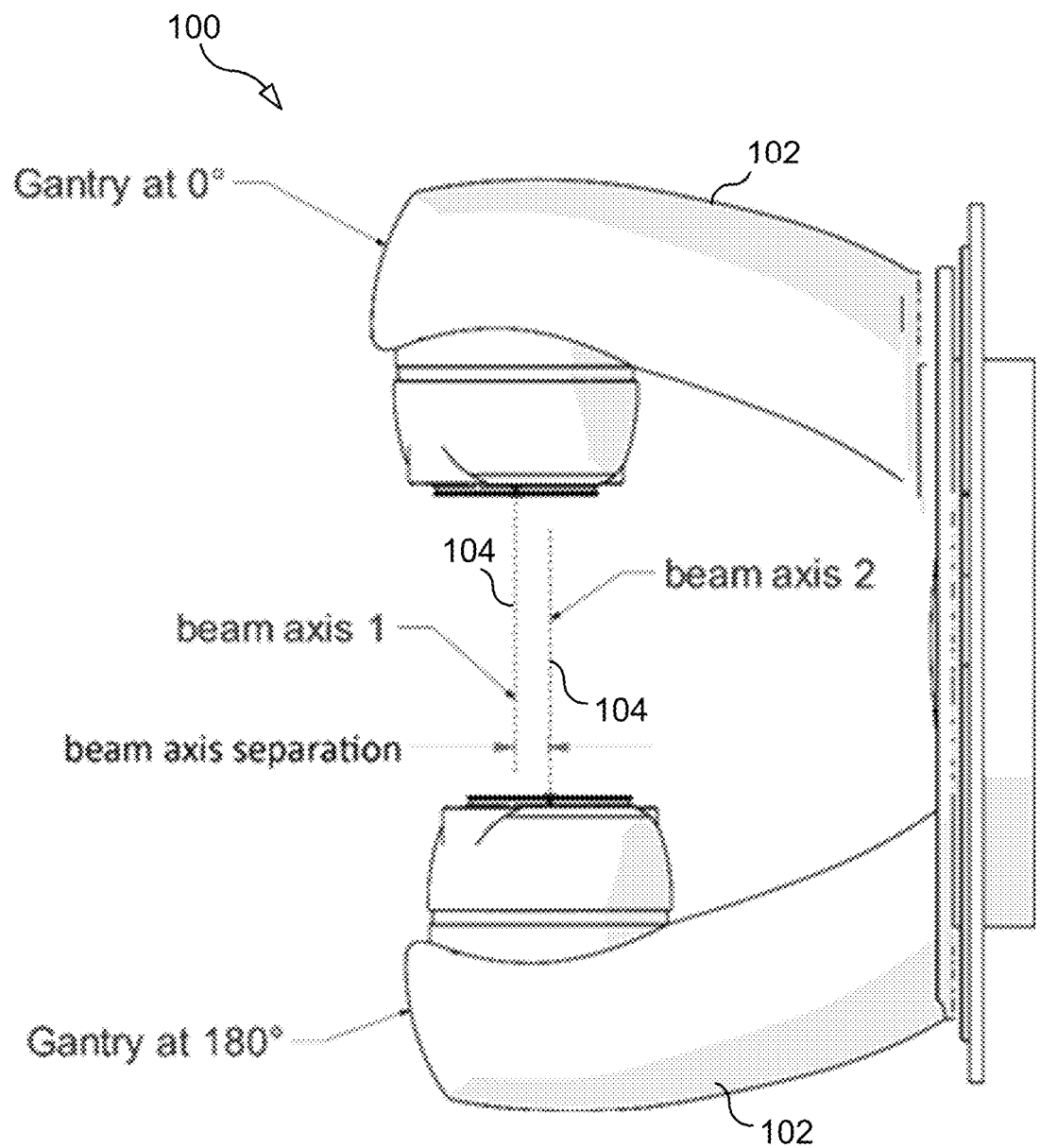
FIG. 3 is illustrates translation of the radiation beam generated by a gantry of a LINAC between when the gantry is at an angle of 0° and when the gantry is at an angle of 180°.
Figure 4:
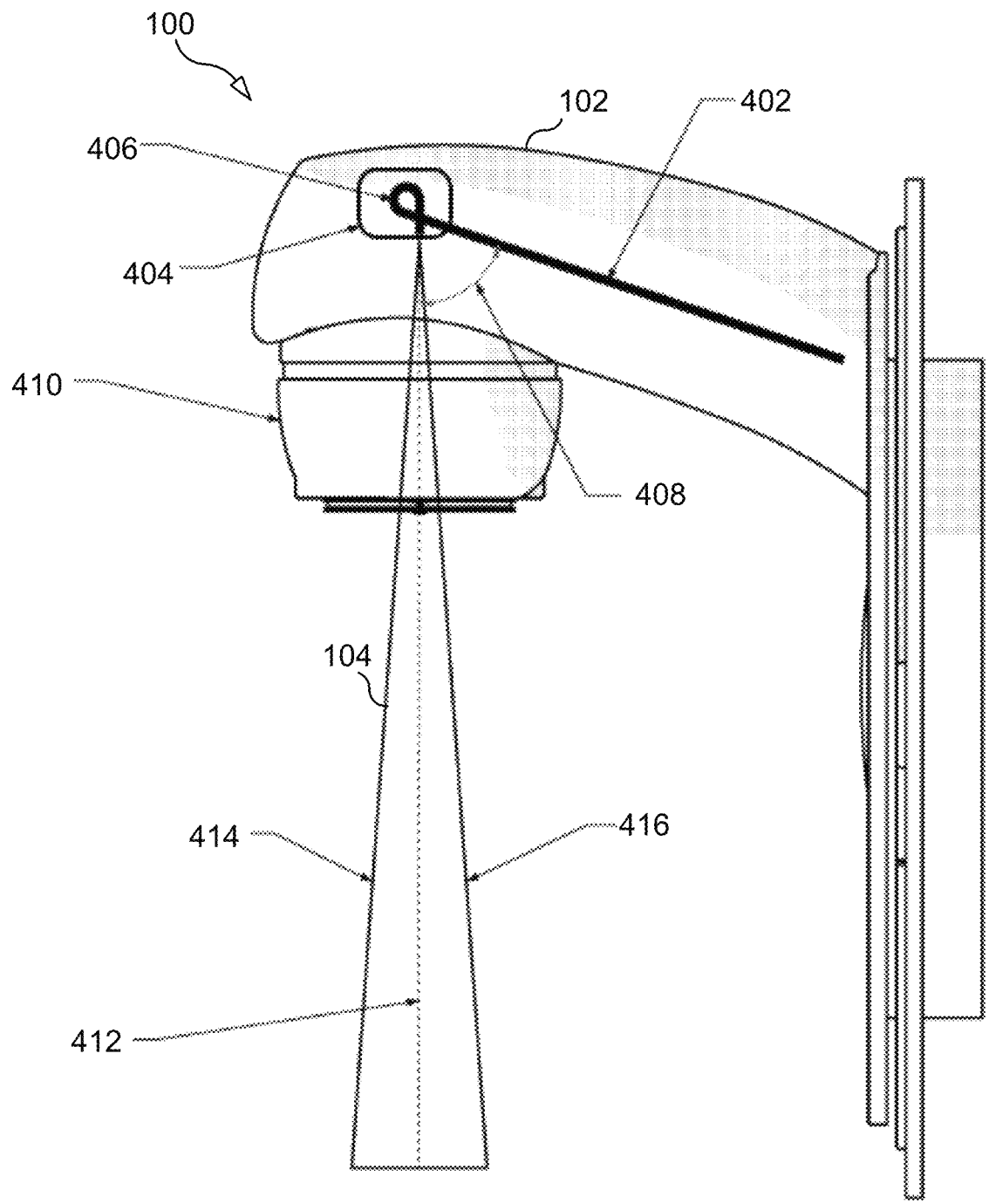
FIG. 4 is a cross-sectional view of a gantry of a LINAC and a radiation beam emitted by the LINAC according to some aspects.

FIG. 4 illustrates a cross-sectional view of a gantry 102 of a linear accelerator (LINAC) 100 and a radiation beam 104 emitted by the LINAC 100 according to some aspects. In some aspects, as shown in FIG. 4, the radiation beam 104 may include a central beam axis 412, a superior beam edge 414, and an inferior beam edge 416. In some aspects, as shown in FIG. 4, the radiation beam 104 may be created in the LINAC 100 by accelerated electrons within a waveguide 402 and bending the electrons downward through an exit window. In some aspects, the electrons may be bent (e.g., downward) with the use of one or more bending magnets 404 (e.g., one or more electro-magnets). In some aspects, the one or more bending magnets 404 allow changes to the angle 408 at which the electron beam 104 is directed onto the target, which also changes the direction the radiation beam 104 takes when exiting a collimator 410 of the LINAC 100. In some aspects, the changes may effectively change the direction of the beam 102 as it travels into the patient during treatment. In some aspects, the magnitude of the radiation beam angle may be controlled by the adjusting a current through the one or more bending magnets 404. Reference numeral 406 denotes the radiation beam in the one or more bending magnets 404.

2.2 Correcting for Gantry Errors Using Modulated Beam Alignment

Figure 5:
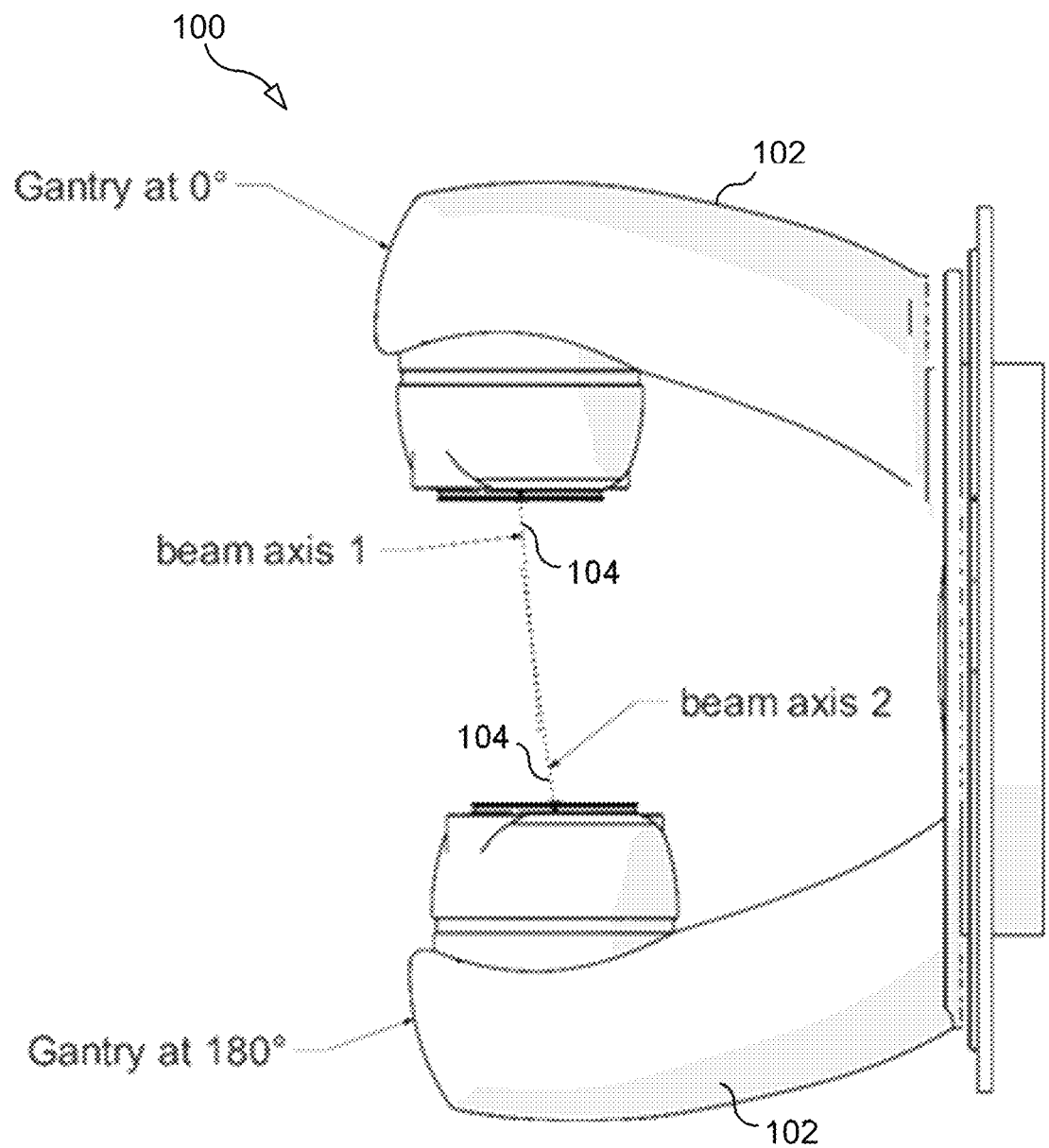
FIG. 5 is a side view of the LINAC shown with the gantry at an angles of 0° and 180° with beam steering is employed to compensate for rotational mechanical inaccuracies of the gantry according to some aspects.

In some aspects, the LINAC 100 (e.g., a controller of the LINAC) may modulate the beam electro-magnet current at each position of the gantry 102 to compensate for any mechanical error in the gantry 102 changing the direction of the radiation beam 104 so that the central beam axis 412 is pointing at the same location in space at each gantry angle. FIG. 5 provides a side view of the LINAC 100 shown with the gantry 102 at an angle of 0° as well as a superimposed view of the gantry 102 at an angle of 180°. As shown in FIG. 5, if beam steering is employed to compensate for rotational mechanical inaccuracies (e.g., mechanical shifts) of the gantry 102, the central beam axis of the radiation beam 104 emitted with the gantry 102 at the angle of 0° and the central beam axis of the radiation beam 104 emitted with the gantry 102 at the angle of 180° can be made to be convergent. In some aspects, the radiation beams 102 may be convergent because the bending magnet currents for the gantry angles of 0° and 180° were selected to align the radiation beam 104 to a direction that enforces convergence of the radiation beam 104 to a single fixed location in space.

2.3 Creating an Aligned Beam

Figure 6:
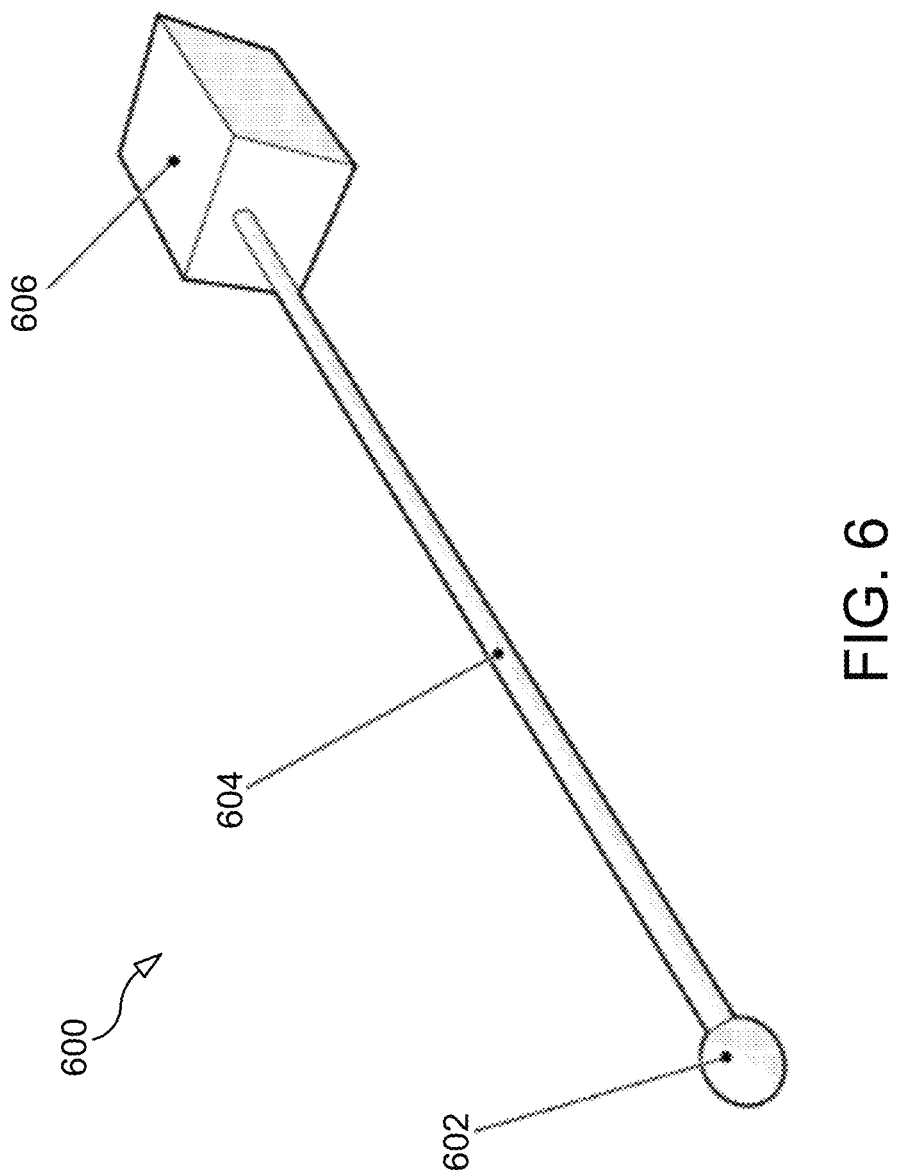
FIG. 6 illustrates a marker assembly according to some aspects.

FIG. 6 illustrates an example of a marker assembly 600 according to some aspects. In some aspects, as shown in FIG. 6, the marker assembly 600 may include a spherical high-density marker 602 (e.g., made of tungsten), a low-density stem 604 (e.g., made of plastic), and a base 606 for positioning. In some aspects, the marker 602 may be a radiation opaque marker.

Figure 7:
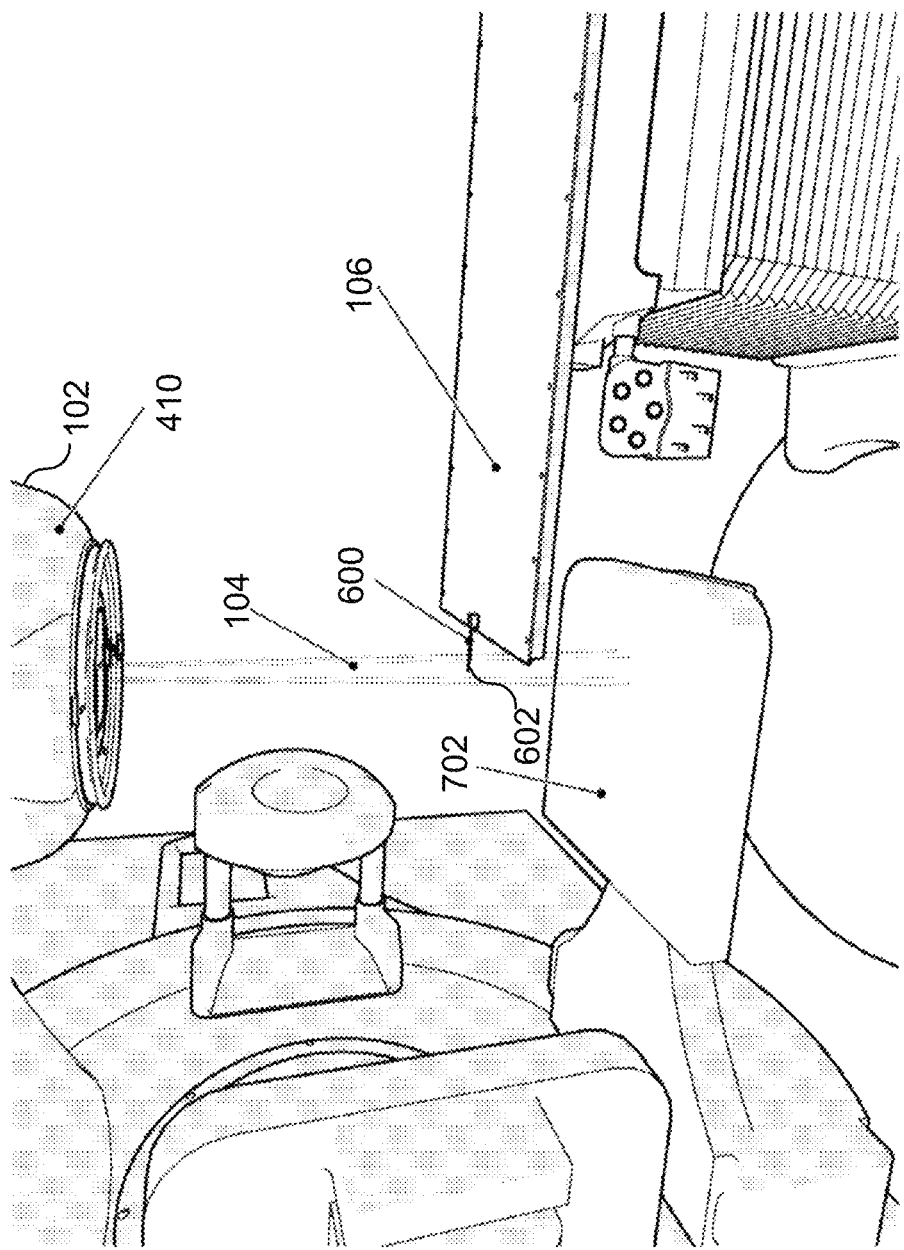
FIG. 7 illustrates a setup for acquiring transmission images to determine whether the radiation beam is aligned according to some aspects.

In some aspects, a radiation beam 104 may be aligned when a target for which the radiation beam 104 is aiming is positioned within the center of the radiation field. FIG. 7 illustrates a setup for acquiring transmission images (e.g., x-ray transmission images) to determine whether the radiation beam 104 is aligned according to some aspects. In some aspects, as shown in FIG. 7, a marker 602 may be placed at a target location. In some aspects, an electronic portal imaging device (EPID) 702 may be used to generate a radiation transmission image of radiation received by the EPID 702. In some aspects, the radiation transmission image may be used to determine whether the radiation beam 104 is aligned by determining whether the centers of the radiation field of the radiation beam 104 and the marker 602 coincide.

Figure 8:
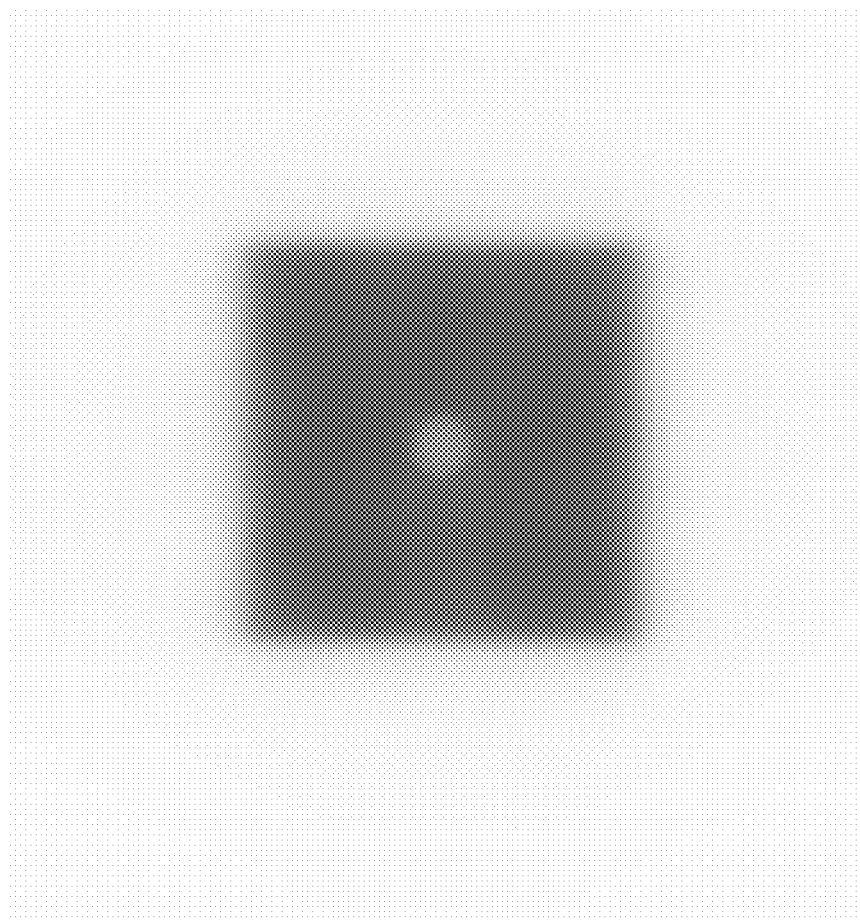
FIG. 8 illustrates an unprocessed radiation transmission image according to some aspects.

FIG. 8 illustrates an example of an unprocessed radiation transmission image generated by the EPID 702 according to some aspects. In some aspects, the radiation transmission image may be an x-ray transmission image. In some aspects, the dark square region may be created by a square radiation field, and the lighter circular inner shape may be created by the shadow of the radiation opaque marker 602 that is positioned within the radiation field. In some aspects, as shown in FIG. 8, in the radiation transmission image, the border of the radiation field and the circle created by the marker 602 may be clearly visible.

Figure 9:
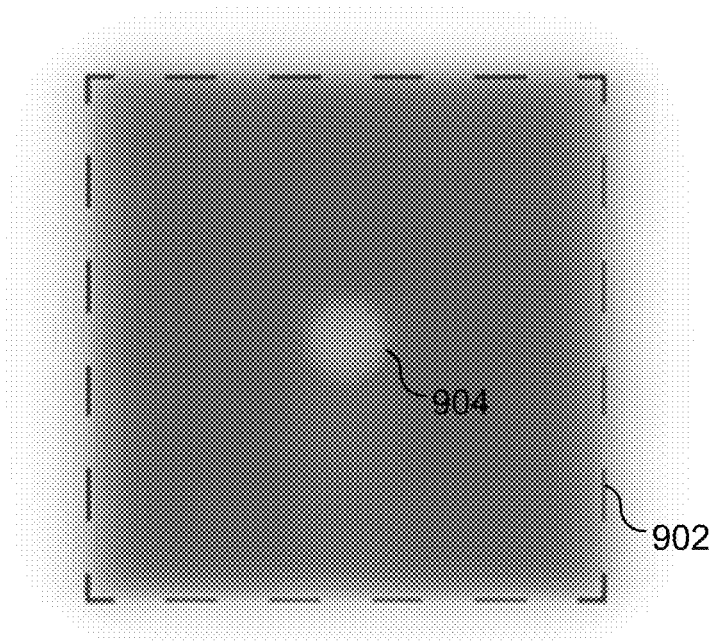
FIG. 9 illustrates a processed radiation transmission image according to some aspects.
Figure 10:
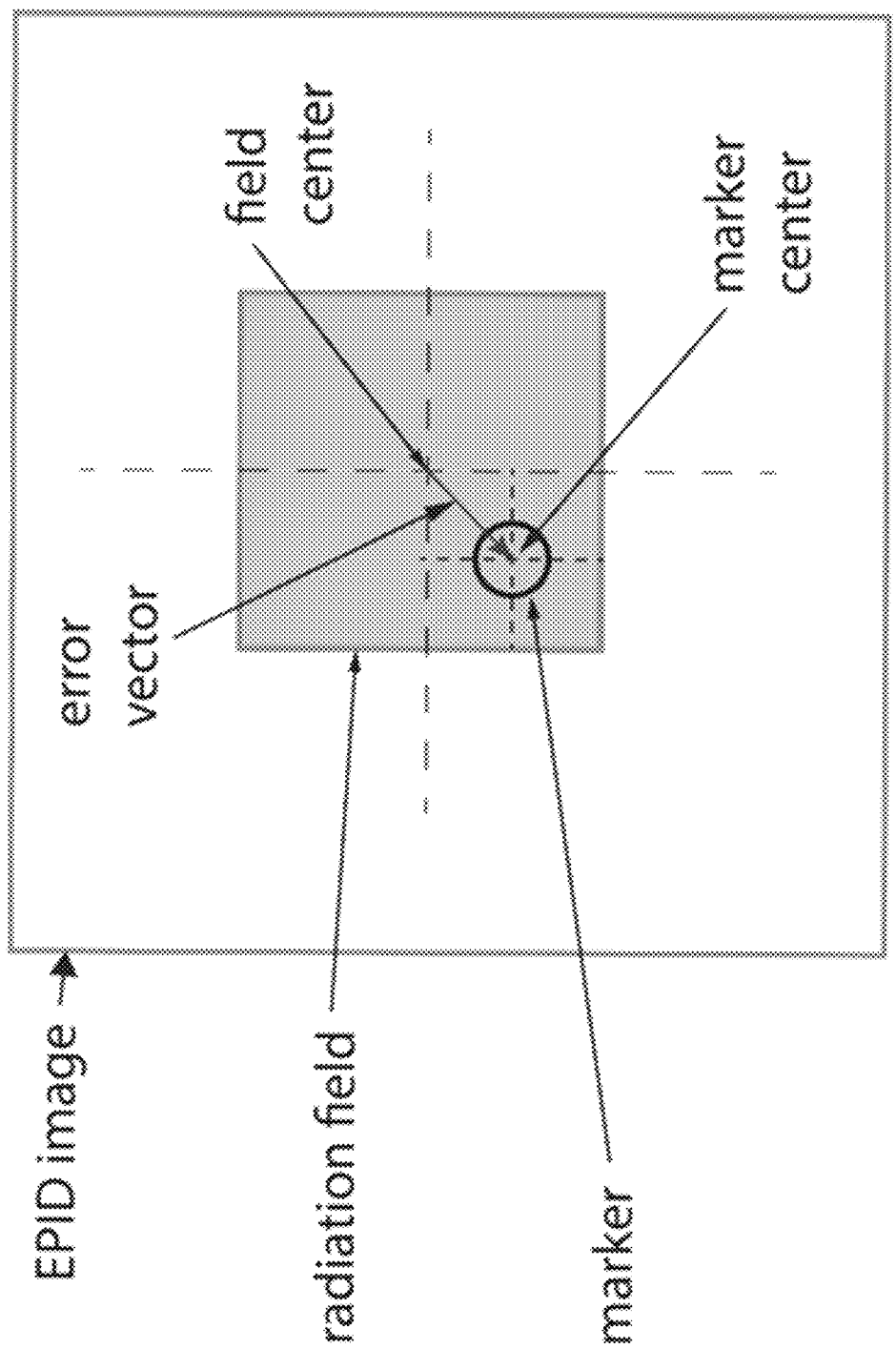
FIG. 10 illustrates a difference in the positions of a radiation opaque marker and radiation field centers according to some aspects.

In some aspects, the LINAC 100 (e.g., a controller of the LINAC 100) may use automated image processing techniques to determine the borders of the radiation field and the circle created by the marker 602. In some aspects, as shown in FIG. 9, the LINAC 100 may detect the border 902 of the radiation field and the border 904 of the marker 602. In some aspects, the LINAC 100 (e.g., a controller of the LINAC 100) may use the borders 902 and 904 of the radiation field and circle created by the marker 602 to calculate the centers of the radiation field and circle. In some aspects, the LINAC 100 may use the calculated centers of the radiation field and circle to determine a marker error vector. In some aspects, as shown in FIG. 10, the marker error vector may be the difference in the positions of the marker and radiation field centers. In some aspects, if the marker error is a non-zero magnitude, the LINAC beam alignment can be adjusted (e.g., by adjusting a current through the one or more bending magnets 404) to move the position of the marker 602 relative to the radiation field until the marker 602 is located at the center of the radiation field at which point the marker error magnitude is minimized.

2.4 Determining the Gantry Dependent Beam Alignment Currents

Figure 11:
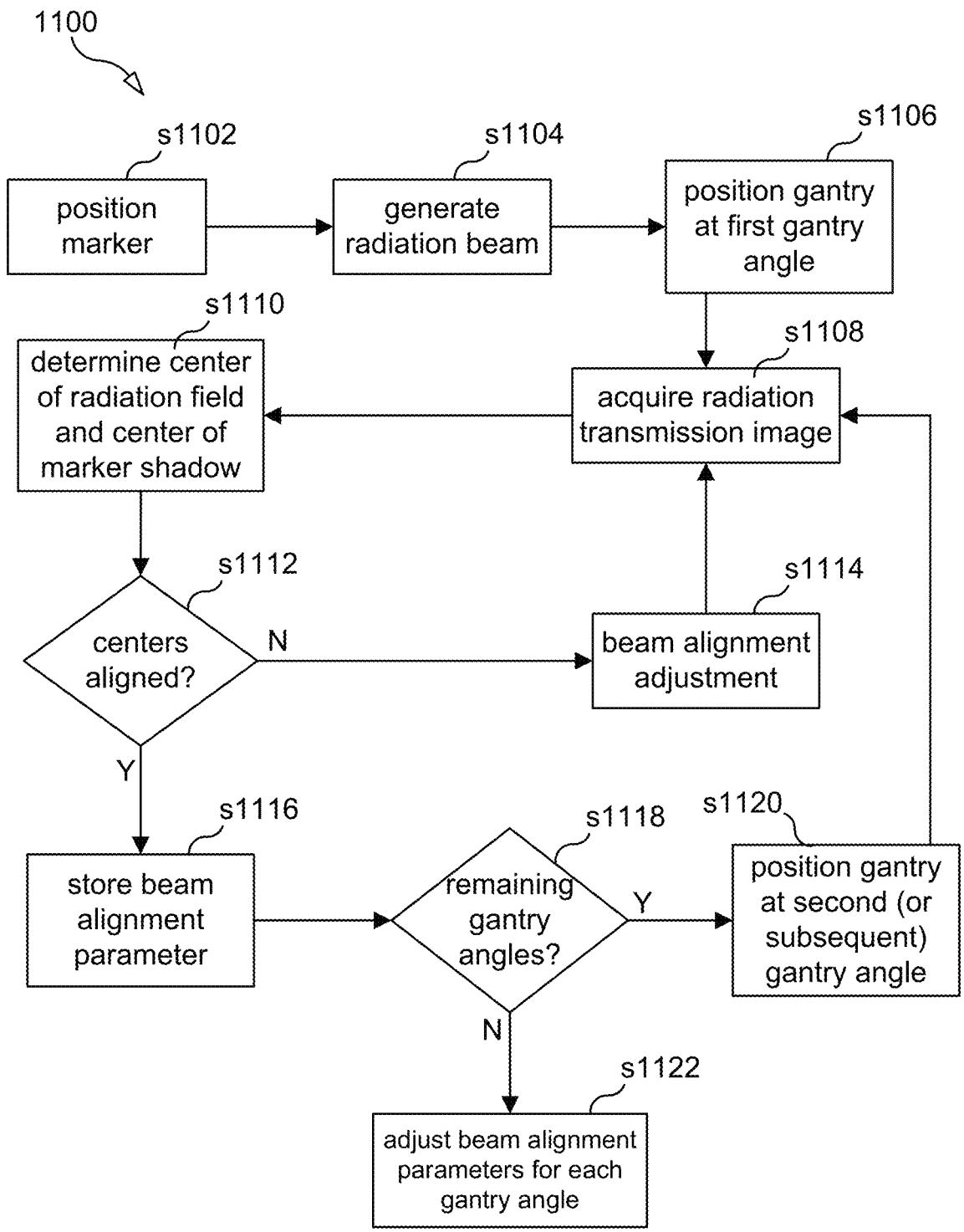
FIG. 11 illustrates a process according to some aspects.

FIG. 11 illustrates a process 1100 to determine gantry dependent beam alignment currents according to some aspects. In some aspects, one or more of the steps of the process 1100 may be performed by the LINAC 100 (e.g., a controller of the LINAC 100). In some aspects, the process 1100 may create a look-up table (LUT) with N number of gantry angle positions as the LUT input and the beam steering currents for that gantry angle as the LUT output. In some aspects, the process 1100 may include applying the beam steering current for a gantry angle when the gantry is at the gantry angle. In some aspects, the process 1100 may additionally or alternatively include employing a parametric fit with N number of gantry angles measured to arrive a formula for determining the beam steering currents for any gantry angle.

In some aspects, the process 1100 may include a step 1102 of positioning a radiation opaque marker 602 (e.g., a spherical marker). In some aspects, the marker 602 may be positioned at a radiation isocenter. In some aspects, the radiation isocenter may be the point in space where the radiation beams 104 intersect when the gantry 102 of the LINAC 100 rotates. In some aspects, the marker 602 may be positioned at the radiation isocenter using room lasers, a mechanical front pointer, and/or machine cross-hairs. In some aspects, the radiation isocenter may be determined and/or the marker 602 may be positioned at the determined radiation isocenter in the manner described in U.S. patent application Ser. No. 16/934,586, filed Jul. 21, 2020, and/or U.S. patent application Ser. No. 16/999,693, filed Aug. 21, 2020, both of which are incorporated herein by reference in their entireties.

In some aspects, the process 1100 may include a step 1104 in which LINAC 100 generates a radiation beam 104. In some aspects, the LINAC may generate the radiation beam 104 using one or more bending magnets 404 and a collimator 410.

In some aspects, the process 1100 may include a step 1106 in which the LINAC 100 positions the gantry 102 at a first gantry angle.

In some aspects, the process 1100 may include a step 1106 in which the LINAC 100 positions the collimator 410 at a first collimator angle (e.g., 0°).

In some aspects, the process 1100 may include a step 1108 in which the LINAC 100 acquires a radiation transmission image indicative of a radiation field of the radiation beam 104 after passing by the radiation opaque marker 602. In some aspects, an electronic portal imaging device (EPID) 702 may generate a radiation transmission image based on radiation received by the EPID 702. In some aspects, the radiation beam 102 generated using the collimator 410 of the LINAC 100 may have a square cross-section, and the radiation field may be a square radiation field. In some alternative aspects, the radiation beam 102 generated using the collimator 410 of the LINAC may have a circular cross-section, and the radiation field may be a circular radiation field.

In some aspects, the process 1100 may include a step 1110 in which the LINAC 100 uses the radiation transmission image to determine a center of the radiation field and a center of a shadow in the radiation field created by the radiation opaque marker 602. In some aspects, the LINAC 100 may use image processing techniques to determine the center of the radiation field in the radiation transmission image and the center of the shadow in the radiation field in the radiation transmission image.

In some aspects, the process 1100 may include a step 1112 in which the LINAC 100 determines whether a center of the radiation field of the radiation beam 104 is at a center of the radiation opaque marker 602 (e.g., within a given tolerance). In some aspects, determining whether the center of the radiation field of the radiation beam 104 is at the center of the radiation opaque marker 602 may include (i) determining a distance between the determined center of the radiation field in the radiation transmission image and the determined center of the shadow in the radiation field in the radiation transmission image and (ii) determining whether the determined distance is less than a distance tolerance threshold. In some aspects, the distance tolerance threshold may depend on the type of treatment being performed. In some aspects, the distance tolerance threshold may be, for example and without limitation, a distance within the range of 0.1 mm to 0.5 mm.

In some aspects, if the center of the radiation field of the radiation beam 104 is determined to be not at the center of the radiation opaque marker 602, the process 1100 may proceed from the step 1112 to a beam alignment adjustment step 1114. In some aspects, the beam alignment adjustment step 1114 may include adjusting a beam alignment parameter of the LINAC 100 to change the direction of the beam. In some aspects, adjusting a beam alignment parameter of the LINAC 100 may include adjusting a current supplied to the one or more bending magnets 404. In some aspects, the process 1100 may proceed from the step 1114 to the step 1108 to repeat the radiation transmission image acquisition step 1108, centers determination step 1110, and center alignment determination steps 1112 with the radiation beam 104 adjusted by to the adjusted beam alignment parameter.

In some aspects, if the center of the radiation field of the radiation beam 104 is determined to be at the center of the radiation opaque marker 602, the process 1100 may proceed from the step 1112 to a step 1116 in which the LINAC 100 stores the beam alignment parameter used when the center of the radiation field of the radiation beam 104 was determined in step 1112 to be at the center of the radiation opaque marker 602 as the optimal beam alignment parameter for the first gantry angle. In some aspects, the optimal beam alignment parameter for the first gantry angle may be stored in a lookup table (LUT).

In some aspects, the process 1100 may include a step 1118 in which the LINAC 100 determines whether any gantry angles remain (e.g., in the LUT) for which optimal beam alignment parameters have not been determined. In some aspects, if any gantry angles remain, the process 1100 may proceed from the step 1118 to a step 1120 in which the LINAC 100 positions the gantry 102 at a second (or subsequent) gantry angle. In some aspects, the process 1100 may proceed from the step 1120 to the step 1106. In some aspects, the process 1110 may repeat the steps 1106, 1108, 1110, 1112, 1114, 1116, and 1118 until no gantry angles remain for optimal beam alignment parameters have not been determined. In some aspects, the LINAC 100 may determine optimal beam alignment parameters for each of N gantry angles. In some aspects, the N gantry angles may be equal to the number of gantry angles at which the LINAC 100 is capable of positioning the gantry 102 (e.g., N may equal 360 for a LINAC 100 capable of positioning the gantry 102 at 360 gantry angles, or N may equal 720 for a LINAC 100 capable of positioning the gantry 102 at 720 gantry angles). In some alternative aspects, the N gantry angles may be fewer than the number of gantry angles at which the LINAC 100 is capable of positioning the gantry 102 (e.g., N may equal 4, 8, 16, 45, 90, or 180, etc. for a LINAC 100 capable of positioning the gantry 102 at 360 gantry angles, or N may equal 4, 8, 16, 45, 90, or 180, etc. for a LINAC 100 capable of positioning the gantry 102 at 720 gantry angles).

In some aspects, if no gantry angles remain, the process 1100 may proceed from the step 1118 to a step 1122 in which the LINAC 100 automatically adjusts the beam alignment parameters for each gantry angle based on the stored optimal beam alignment parameters (e.g., during a radiation therapy treatment). In some aspects, for a gantry angle that is not one of the N gantry angles for which for which optimal beam alignment parameters have been determined using radiation transmission images, the LINAC 100 may use one or more of the optimal beam alignment parameters for one or more of the N gantry angles in proximity to the gantry angle (e.g., the optimal beam alignment parameters for the two of the N gantry angles adjacent to the gantry angle) to calculate an optimal beam alignment parameter for the gantry angle (e.g., using a mathematical process such as, for example and without limitation, averaging or linear or polynomial interpolation). In some aspects (e.g., some aspects in which the N gantry angles for which optimal beam alignment parameters have not been determined are fewer than the number of gantry angles at which the LINAC 100 is capable of positioning the gantry 102), the process 1100 may include the LINAC 100 using the N stored optimal beam alignment parameters for the N gantry angles measured to determine a formula for determining beam alignment parameters (e.g., beam steering currents) for any gantry angle at which the LINAC 100 is capable of positioning the gantry 102 and using the formula to adjust beam alignment parameters as the gantry angle changes. In some aspects, the LINAC 100 may employ mathematical process such as, for example, and without limitation, parametric curve fitting or interpolation to determine the formula.

2.5 Variation for Poorly Calibrated Collimators

In some aspects, the collimation system of a LINAC 100, which defines the radiation field of the radiation beam 104, may be poorly calibrated. If the collimation system is poorly calibrated, rotation of the collimator 410 by 180° will result in a different field location. In some aspects, the process 1100 may account for poor calibration of the collimation system by capturing two or more radiation transmission images for each of the measured beam alignment parameters. In some aspects, the two or more radiation transmission images may have different collimator angles (e.g., collimator angles separated by 180°). In some aspects, the radiation field center determined in step 1110 may be the average of the radiation field centers found at the two or more collimator angles (e.g., 0° and 180°). In some aspects, if the collimator 410 is calibrated well, the two or more radiation field centers will be the same, and the average between the two or more will be identical to the field center if only one radiation transmission image were acquired.

Figure 12:
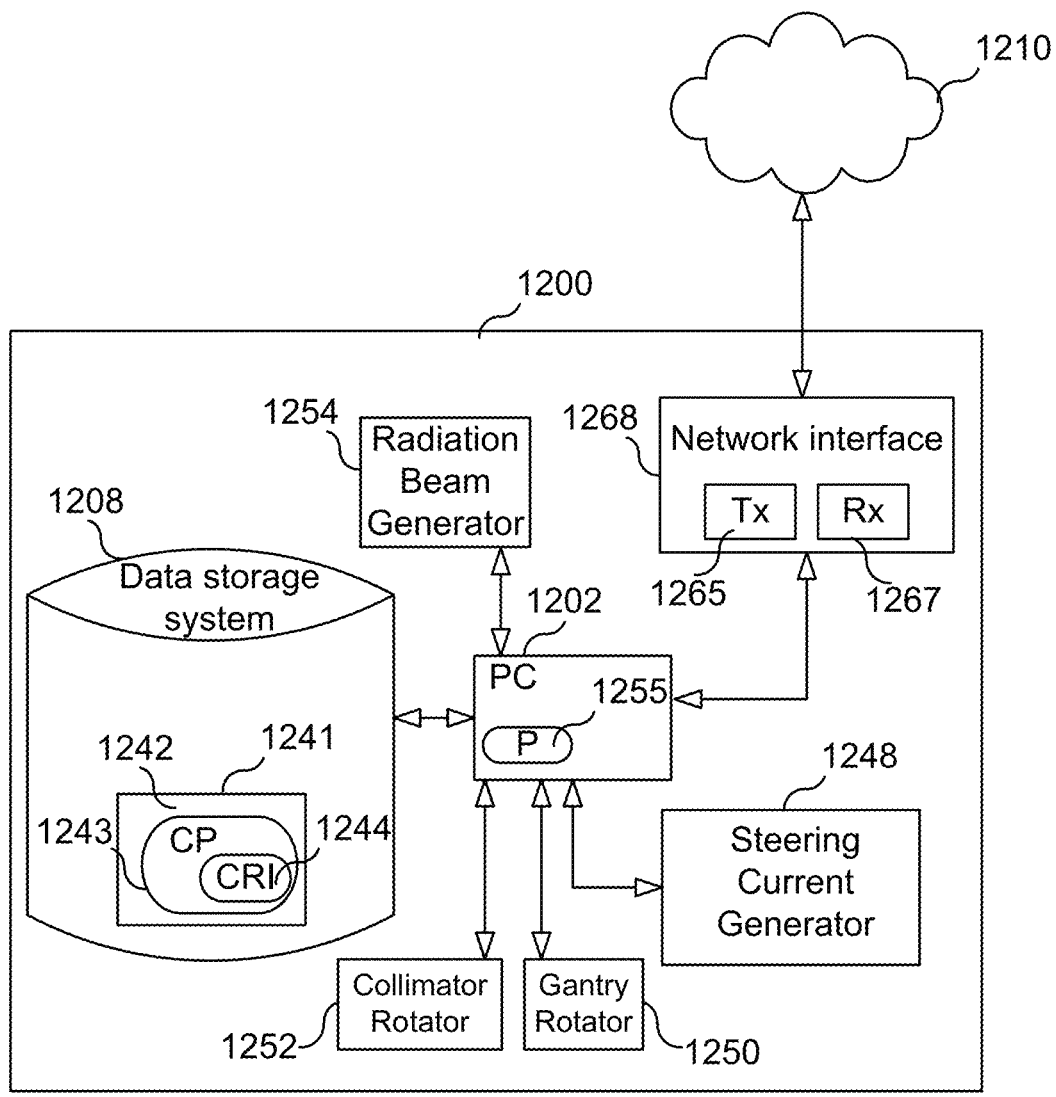
FIG. 12 illustrates a controller of a LINAC according to some aspects.

FIG. 12 is a block diagram of a controller 1200 of a LINAC 100 according to some aspects. As shown in FIG. 12, the controller 1200 may comprise: processing circuitry (PC) 1202, which may include one or more processors (P) 1255 (e.g., one or more general purpose microprocessors and/or one or more other processors, such as an application specific integrated circuit (ASIC), field-programmable gate arrays (FPGAs), and the like), which processors may be co-located in a single housing or in a single data center or may be geographically distributed (i.e., the system may be a distributed computing apparatus); a network interface 1268 comprising a transmitter (Tx) 1265 and a receiver (Rx) 1267 for enabling the controller 1200 to transmit data to and receive data from other nodes connected to a network 1210 (e.g., an Internet Protocol (IP) network) to which network interface 1268 is connected; a steering current generator 1248 configured to supply beam steering currents for the one or more bending magnets 404; a gantry rotator 1250; a collimator rotator 1252 configured to rotate the collimator 410; a radiation beam generator 1254 configured to generate the electron beam in the waveguide 402; and a local storage unit (a.k.a., "data storage system") 1208, which may include one or more non-volatile storage devices and/or one or more volatile storage devices. In aspects where PC 1202 includes a programmable processor, a computer program product (CPP) 1241 may be provided. In some aspects, the CPP 1241 may include a computer readable medium (CRM) 1242 storing a computer program (CP) 1243 comprising computer readable instructions (CRI) 1244. In some aspects, the CRM 1242 may be a non-transitory computer readable medium, such as, magnetic media (e.g., a hard disk), optical media, memory devices (e.g., random access memory, flash memory), and the like. In some aspects, the CRI 1244 of computer program 1243 may be configured such that when executed by PC 1202, the CRI causes the LINAC 100 to perform steps described herein (e.g., one or more steps described herein with reference to the flowcharts herein). In other aspects, the controller 1200 may be configured to perform steps described herein without the need for code. That is, for example, the PC 1202 may consist merely of one or more ASICs. Hence, the features of the aspects described herein may be implemented in hardware and/or software.

While various embodiments are described herein, it should be understood that they have been presented by way of example only, and not limitation. Thus, the breadth and scope of this disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

Having described preferred embodiments which serve to illustrate various concepts, structures and techniques which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

What is claimed is:

1. A method comprising:
    using one or more bending magnets and a collimator of a linear accelerator (LINAC) to generate a radiation beam;
    using the LINAC to position a gantry at a first gantry angle;
    with the gantry positioned at the first gantry angle, acquiring a first radiation transmission image indicative of a radiation field of the radiation beam after passing by a radiation opaque marker;
    using the first radiation transmission image to determine a center of the radiation field of the radiation beam and a center of a shadow of the radiation opaque marker in the radiation field of the radiation beam;
    determining that the center of the radiation field of the radiation beam is not at the center of the shadow of the radiation opaque marker;
    if the center of the radiation field of the radiation beam is determined to not be at the center of the shadow of the radiation opaque marker, adjusting the radiation beam by adjusting a beam alignment parameter and repeating the radiation transmission image acquisition step and the centers determination step with the adjusted radiation beam and the gantry positioned at the first gantry angle until a center of the radiation field of the adjusted radiation beam is determined to be at the center of the shadow of the radiation opaque marker, wherein adjusting the beam alignment parameter adjusts a current supplied by the LINAC to the one or more bending magnets;
    if the center of the radiation field of the adjusted radiation beam is determined to be at the center of the shadow of the radiation opaque marker, storing the adjusted beam alignment parameter as an optimal beam alignment parameter for the first gantry angle; and
    using the adjusted beam alignment parameter stored as the optimal beam alignment parameter for the first gantry angle to adjust the current supplied by the LINAC to the one or more bending magnets when the gantry of the LINAC rotates to the first gantry angle.

2. The method of claim 1, further comprising positioning the radiation opaque marker.

3. The method of claim 1, further comprising positioning the radiation opaque marker at a radiation isocenter, wherein the radiation isocenter is a point in space where radiation beams generated by the LINAC intersect when the gantry of the LINAC rotates.

4. The method of claim 3, further comprising determining the radiation isocenter.

5. The method of claim 1, further comprising using an electronic portal imaging device (EPID) to generate the first radiation transmission image based on radiation received by the EPID.

6. The method of claim 1, wherein the radiation opaque marker is a spherical radiation opaque marker.

7. The method of claim 1, wherein the radiation field of the radiation beam is a square radiation beam.

8. The method of claim 1, wherein determining that the center of the radiation field of the radiation beam is not at the center of the shadow of the radiation opaque marker comprises:
   determining a distance between the center of the radiation field of the radiation beam and the center of the shadow of the radiation opaque marker; and
   determining that the distance is greater than a distance tolerance threshold.

9. The method of claim 1, wherein determining that the center of the radiation field of the adjusted radiation beam is at the center of the shadow of the radiation opaque marker comprises:
   determining a distance between the center of the radiation field of the adjusted radiation beam and the center of the shadow of the radiation opaque marker; and
   determining that the distance is less than a distance tolerance threshold.

10. The method of claim 1, wherein the adjusted beam alignment parameter is stored as the optimal beam alignment parameter for the first gantry angle in a lookup table.

11. The method of claim 1, further comprising:
   using the LINAC to position the gantry at a second gantry angle;
   with the gantry positioned at the second gantry angle, acquiring a second radiation transmission image indicative of the radiation field of the radiation beam after passing by the radiation opaque marker;
   using the second radiation transmission image to determine a center of the radiation field of the radiation beam and a center of a shadow of the radiation opaque marker in the radiation field of the radiation beam;
   determining that the center of the radiation field of the radiation beam is not at the center of the shadow of the radiation opaque marker;
   if the center of the radiation field of the radiation beam is determined to not be at the center of the shadow of the radiation opaque marker, adjusting the radiation beam by adjusting a beam alignment parameter and repeating the radiation transmission image acquisition step and the centers determination step with the adjusted radiation beam and the gantry positioned at the second gantry angle until a center of the radiation field of the adjusted radiation beam is determined to be at the center of the shadow of the radiation opaque marker, wherein adjusting the beam alignment parameter adjusts the current supplied by the LINAC to the one or more bending magnets;
   if the center of the radiation field of the adjusted radiation beam is determined to be at the center of the shadow of the radiation opaque marker, storing the adjusted beam alignment parameter as an optimal beam alignment parameter for the second gantry angle; and
   using the adjusted beam alignment parameter stored as the optimal beam alignment parameter for the second gantry angle to adjust the current supplied by the LINAC to the one or more bending magnets when the gantry of the LINAC rotates to the second gantry angle.

12. The method of claim 1, further comprising, for each of N gantry angles:
   using the LINAC to position the gantry at a gantry angle of the N gantry angles;
   determining an optimal beam alignment parameter for the gantry angle of the N gantry angles, wherein the optimal beam alignment parameter adjusts the current supplied by the LINAC to the one or more bending magnets such that a center of the radiation field of the radiation beam is at a center of the radiation opaque marker when the gantry is at the gantry angle of the N gantry angle; and
   storing the optimal beam alignment parameter for the gantry angle of the N gantry angles.

13. The method of claim 12, further comprising using the N optimal beam alignment parameters stored for the N gantry angles to adjust the current supplied by the LINAC to the one or more bending magnets during rotation of the gantry.

14. The method of claim 12, further comprising:
   determining a formula for determining beam alignment parameters based on the N optimal beam alignment parameters stored for the N gantry angles; and
   using the LINAC to adjust the current supplied by the LINAC to the one or more bending magnets based on the formula as the gantry rotates.

15. The method of claim 14, wherein the LINAC employs parametric curve fitting or interpolation to determine the formula.

16. The method of claim 1, further comprising:
   using the LINAC to position the collimator at least at a first collimator angle and a second collimator angle, wherein the first radiation transmission image is acquired with the gantry positioned at the first gantry angle and the collimator position at the first collimator angle, and the second collimator angle is different than the first collimator angle;
   with the gantry positioned at the first gantry angle and the collimator positioned at the second collimator angle, acquiring an additional radiation transmission image indicative of a radiation field of the radiation beam after passing by the radiation opaque marker;
   wherein the first radiation transmission image and the additional transmission image are used to determine the center of the radiation field of the radiation beam.

17. The method of claim 16, wherein the center of the radiation field of the radiation beam is determined by averaging the center of the radiation field in the first radiation transmission field image and the center of the radiation field in the additional radiation transmission field image.

18. A linear accelerator (LINAC) comprising:
   a gantry;
   one or more bending magnets;
   a collimator; and
   a controller configured to cause the LINAC to:
      use the one or more bending magnets and the collimator to generate a radiation beam;
      position the gantry at a first gantry angle;
      with the gantry positioned at the first gantry angle, acquire a first radiation transmission image indicative of a radiation field of the radiation beam after passing by a radiation opaque marker;
      use the first radiation transmission image to determine a center of the radiation field of the radiation beam and a center of a shadow of the radiation opaque marker in the radiation field of the radiation beam;

determine that the center of the radiation field of the radiation beam is not at the center of the shadow of the radiation opaque marker;

if the center of the radiation field of the radiation beam is determined to not be at the center of the shadow of the radiation opaque marker, adjust the radiation beam by adjusting a beam alignment parameter and repeat the radiation transmission image acquisition step and the centers determination step with the adjusted radiation beam and the gantry positioned at the first gantry angle until a center of the radiation field of the adjusted radiation beam is determined to be at the center of the shadow of the radiation opaque marker, wherein adjusting the beam alignment parameter adjusts a current supplied to the one or more bending magnets;

if the center of the radiation field of the adjusted radiation beam is determined to be at the center of the shadow of the radiation opaque marker, store the adjusted beam alignment parameter as an optimal beam alignment parameter for the first gantry angle; and use the adjusted beam alignment parameter stored as the optimal beam alignment parameter for the first gantry angle to adjust the current supplied by the LINAC to the one or more bending magnets when the gantry of the LINAC rotates to the first gantry angle.

19. The apparatus of claim 18, wherein the controller is further configured to cause the LINAC to:

position the gantry at a second gantry angle;

with the gantry positioned at the second gantry angle, acquire a second radiation transmission image indicative of the radiation field of the radiation beam after passing by the radiation opaque marker;

use the second radiation transmission image to determine a center of the radiation field of the radiation beam and a center of a shadow of the radiation opaque marker in the radiation field of the radiation beam;

determine that the center of the radiation field of the radiation beam is not at the center of the shadow of the radiation opaque marker;

if the center of the radiation field of the radiation beam is determined to not be at the center of the shadow of the radiation opaque marker, adjust the radiation beam by adjusting a beam alignment parameter and repeating the radiation transmission image acquisition step and the centers determination step with the adjusted radiation beam and the gantry positioned at the second gantry angle until a center of the radiation field of the adjusted radiation beam is determined to be at the center of the shadow of the radiation opaque marker, wherein adjusting the beam alignment parameter adjusts the current supplied by the LINAC to the one or more bending magnets;

if the center of the radiation field of the adjusted radiation beam is determined to be at the center of the shadow of the radiation opaque marker, store the adjusted beam alignment parameter as an optimal beam alignment parameter for the second gantry angle; and use the adjusted beam alignment parameter stored as the optimal beam alignment parameter for the second gantry angle to adjust the current supplied by the LINAC to the one or more bending magnets when the gantry of the LINAC rotates to the second gantry angle.

20. The apparatus of claim 18, wherein the controller is further configured to cause the LINAC to, for each of N gantry angles:

position the gantry at a gantry angle of the N gantry angles;

determine an optimal beam alignment parameter for the gantry angle of the N gantry angles, wherein the optimal beam alignment parameter adjusts the current supplied by the LINAC to the one or more bending magnets such that a center of the radiation field of the radiation beam is at a center of the radiation opaque marker when the gantry is at the gantry angle of the N gantry angle; and store the optimal beam alignment parameter for the gantry angle of the N gantry angles.

* * * * *